United States Patent
Mario et al.

(10) Patent No.: US 7,799,095 B2
(45) Date of Patent: Sep. 21, 2010

(54) ANHYDROUS COMPOSITION COMPRISING AT LEAST ONE OXIDATION DYE, AT LEAST ONE COMPLEX OF HYDROGEN PEROXIDE, AND A SPECIFIC POLYMER, AND A COLORING PROCESS USING THE SAME

(75) Inventors: Maud Mario, Paris (FR); Patricia Desenne, Bois Colombes (FR); Jean-Marie Millequant, Saint-maur des Fosses (FR)

(73) Assignee: L'Oreal S.A., Paris (FR)

( * ) Notice: Subject to any disclaimer, the term of this patent is extended or adjusted under 35 U.S.C. 154(b) by 73 days.

(21) Appl. No.: 12/215,422

(22) Filed: Jun. 27, 2008

(65) Prior Publication Data
US 2009/0151087 A1 Jun. 18, 2009

Related U.S. Application Data

(60) Provisional application No. 60/929,814, filed on Jul. 13, 2007, provisional application No. 60/929,815, filed on Jul. 13, 2007.

(30) Foreign Application Priority Data
Jun. 29, 2007 (FR) .................................. 07 56171
Jun. 29, 2007 (FR) .................................. 07 56173

(51) Int. Cl.
*A61Q 5/10* (2006.01)
(52) U.S. Cl. ........................ 8/405; 8/406; 8/524; 8/552; 8/553; 8/617; 8/619; 8/620; 8/649
(58) Field of Classification Search ............... 8/405, 8/406, 524, 552, 553, 617, 619, 649
See application file for complete search history.

(56) References Cited

U.S. PATENT DOCUMENTS

| | | | |
|---|---|---|---|
| 4,826,681 A | 5/1989 | Jacquet et al. | |
| 5,674,436 A | 10/1997 | Breitenbach et al. | |
| 5,753,770 A | 5/1998 | Breitenbach et al. | |
| 5,945,032 A | 8/1999 | Breitenbach et al. | |
| 2003/0172469 A1 | 9/2003 | Schulze zur Wiesche et al. | |
| 2006/0236469 A1* | 10/2006 | Bone et al. ............... | 8/405 |
| 2006/0254001 A1 | 11/2006 | Hoeffkes et al. | |
| 2007/0071695 A1 | 3/2007 | Chopra et al. | |
| 2007/0174977 A1 | 8/2007 | Plos | |

FOREIGN PATENT DOCUMENTS

| | | |
|---|---|---|
| DE | 43 44 131 A1 | 6/1995 |
| DE | 195 45 380 A1 | 6/1997 |
| DE | 199 61 910 | 6/2001 |
| EP | 0 193 471 A1 | 9/1986 |
| EP | 0 714 919 A2 | 6/1996 |
| EP | 0 832 846 A2 | 4/1998 |
| EP | 1 747 774 | 1/2007 |
| WO | WO 2004/087086 A2 | 10/2004 |
| WO | WO 2005/021427 A1 | 3/2005 |
| WO | WO 2007/037961 A1 | 4/2007 |

OTHER PUBLICATIONS

Zviak Charles: "Science des traitement capillaires" 1988, Masson, Paris, XP002467880, pp. 271-273.
French Search Report for FR 1756171 (French priority application for U.S. Appl. No. 12/215,422), dated Feb. 19, 2008.
French Search Report for FR 1756173 (French priority application for U.S. Appl. No. 12/215,422), dated Feb. 19, 2008.
English Derwent Abstract for DE 195 45 380, (1997).
English Derwent Abstract for WO 2004/087086, (2004).
European Search Report for EP 08 15 9102, dated Nov. 13, 2008.

* cited by examiner

*Primary Examiner*—Eisa B Elhilo
(74) *Attorney, Agent, or Firm*—Finnegan, Henderson, Farabow, Garrett & Dunner LLP

(57) ABSTRACT

A subject-matter of the present invention is an anhydrous composition in the form of a paste or in the pulverulent form for the coloring of the keratinous human fibers comprising at least one oxidation dye, at least one complex of hydrogen peroxide and a specific polymer and at least one alkaline agent. A subject-matter of the invention is likewise a method for coloring keratinous fibers in which the following stages are carried out: —The above mentioned anhydrous composition is mixed with an aqueous composition advantageously devoid of hydrogen peroxide, and the resulting composition is applied to the keratinous fibers, the composition is left to stand and the fibers are rinsed.

15 Claims, No Drawings

ANHYDROUS COMPOSITION COMPRISING AT LEAST ONE OXIDATION DYE, AT LEAST ONE COMPLEX OF HYDROGEN PEROXIDE, AND A SPECIFIC POLYMER, AND A COLORING PROCESS USING THE SAME

CROSS-REFERENCE TO RELATED APPLICATIONS

This application claims benefit of priority under 35 U.S.C. §119 to French Patent Application No. FR 0756171, filed Jun. 29, 2007, and French Patent Application No. 0756173, filed Jun. 29, 2007, and the benefit of U.S. Provisional Application No. 60/929,814, filed Jul. 13, 2007, and U.S. Provisional Application No. 60/929,815, filed Jul. 13, 2007, the content of all of which is incorporated herein by reference.

The subject-matter of the present invention is an anhydrous composition for the colouring of human keratinous fibres comprising at least one oxidation dye, at least one hydrogen peroxide complex and a specific polymer, at least one alkaline agent, and also a method for colouring keratinous fibres in which the anhydrous composition is mixed with at least water before applying it to the said fibres.

Mention may be made, among methods for colouring human keratinous fibres, such as the hair, of oxidation or permanent dyeing. More particularly, this colouring method employs one or more oxidation dyes, more particularly one or more oxidation bases, optionally in combination with one or more couplers.

Usually, oxidation bases are chosen from ortho- or para-phenylenediamines, ortho- or para-aminophenols, and heterocyclic compounds. These oxidation bases are colourless or weakly coloured compounds which, in combination with oxidizing products, make it possible to arrive at coloured entities by an oxidative coupling process.

The shades obtained with these oxidation bases can very often be varied by combining them with one or more couplers, the latter being chosen in particular from aromatic meta-diamines, meta-aminophenols, meta-diphenols and certain heterocyclic compounds, such as indole compounds.

The variety of the molecules employed as oxidation bases and couplers makes it possible to obtain a rich palette of colours.

The colouring process employing oxidation dyes is usually carried out starting from several compositions, at least one dyeing composition and at least one oxidizing composition, which are mixed at the time of use immediately before the application of the final composition to the fibres. This is because it is impossible to store, in the same composition, all the ingredients except the water, in order to prevent decomposition of the hydrogen peroxide in an alkaline aqueous medium, which brings about the coupling reaction of the oxidation bases and couplers.

Thus, according to the normal practice, the dyeing composition or compositions, on the one hand, and the aqueous oxidizing composition, which exhibits an acid pH in order to guarantee the stability of the hydrogen peroxide, on the other hand, are stored separately and are only brought into contact at the moment of use.

The need to employ several compositions results first of all in disadvantages inherent in the storage of several compositions, with a greater storage surface area.

Furthermore, this results in the need to measure out the compositions before bringing them into contact. It is possible, in order to overcome this disadvantage, to provide for the use of kits (or multicompartment devices) but this, despite everything, complicates the use of the compositions and increases the cost. Furthermore, in some cases, the dyeing and oxidizing compositions are provided in different formulation forms, such as, for example, powders, pastes or creams, for example, which can complicate the mixing and the production of a homogeneous final composition.

Finally, the fact of using separate oxidizing compositions makes it necessary to handle fairly concentrated oxidizing solutions.

The aim of the present invention is thus to provide a composition which simultaneously comprises all the ingredients required for carrying out an oxidation dyeing process and which is stable on storage.

This composition makes it possible both to regulate the problem of storage by limiting the number of compositions to be stored and to greatly facilitate the use thereof as it would then no longer be necessary to mix it with an oxidizing composition prior to its use but simply with water, in the most advantageous cases.

These aims and others are achieved by the present invention, a subject-matter of which is thus an anhydrous composition for the colouring of human keratinous fibres, in particular the hair, comprising:

one or more oxidation dye precursors;
one or more complexes of hydrogen peroxide and of a polymer comprising, as monomer, at least one vinyl heterocyclic monomer;
one or more alkaline agents.

A subject-matter of the present invention is likewise a method for colouring human keratinous fibres, in particular the hair, in which the following stages are carried out:

the composition according to the invention is mixed with an aqueous composition and the resulting composition is applied to the keratinous fibres,
the composition is left to stand,
the fibres are rinsed.

Other characteristics, aspects, objects and advantages of the invention will become more clearly apparent on reading the description which follows.

It should be noted that, in that which follows and unless otherwise indicated, the limits of a range of values are included in this range.

According to the invention, a composition is said to be anhydrous when it comprises a water content of at most 1% by weight, with respect to the weight of the composition. Preferably, this water content is at most 0.5% by weight, with respect to the weight of the composition.

More particularly, the water content varies from 0 to 1% by weight and preferably from 0 to 0.5% by weight, with respect to the total weight of the composition.

According to a first embodiment of the invention, the composition is provided in the form of a paste.

Within the meaning of the present invention, the term "anhydrous paste" is understood to mean an anhydrous composition exhibiting a viscosity of greater than 5 poises and preferably greater than 10 poises, measured at 25° C. and at a shear rate of 1 $s^{-1}$; it being possible for this viscosity to be determined by means of a cone/plate rheometer.

According to a second embodiment of the invention, the anhydrous composition is provided in the pulverulent form.

Advantageously, the anhydrous composition is essentially devoid of dust (or fine particles). In other words, the particle size distribution of the particles is such that the level by weight of the particles which have a size of less than or equal to 65 microns (level of fines) is advantageously less than or equal to 5%, preferably less than 2% and more particularly less than 1% (size of the particles evaluated by means of a Retsch AS 200 Digit particle sizer; vibration height: 1.25 mm/sieving time: 5 minutes). Advantageously, the size of the particles is between 65 μm and 2 mm.

As was indicated above, the composition comprises one or more oxidation dyes, namely one or more oxidation bases, optionally in combination with one or more couplers.

By way of example, the oxidation bases are chosen from para-phenylenediamines, bisphenylalkylenediamines, para-aminophenols, ortho-aminophenols, heterocyclic bases and their addition salts.

Mention may be made, among para-phenylenediamines, by way of example, of para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-(β-hydroxyethyl)-para-phenylene-diamine, 2-fluoro-para-phenylenediamine, 2-isopropyl-para-phenylenediamine, N-(β-hydroxypropyl)-para-phenylenediamine, 2-hydroxymethyl-para-phenylene-diamine, N,N-dimethyl-3-methyl-para-phenylenediamine, N,N-(ethyl, β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(β-hydroxyethyloxy)-para-phenylene-diamine, 2-(β-acetylaminoethyloxy)-para-phenylene-diamine, N—(β-methoxyethyl)-para-phenylenediamine, 4-aminophenylpyrrolidine, 2-thienyl-para-phenylene-diamine, 2-(β-hydroxyethylamino)-5-aminotoluene, 3-hydroxy-1-(4'-aminophenyl)pyrrolidine and their addition salts with an acid.

Among the para-phenylenediamines mentioned above, para-phenylenediamine, para-toluylenediamine, 2-isopropyl-para-phenylenediamine, 2-(β-hydroxyethyl)-para-phenylenediamine, 2-(β-hydroxyethyloxy)-para-phenylene-diamine, 2,6-dimethyl-para-phenylenediamine, 2,6-di-ethyl-para-phenylenediamine, 2,3-dimethyl-para-phenylenediamine, N,N-bis(β-hydroxyethyl)-para-phenylenediamine, 2-chloro-para-phenylenediamine, 2-(β-acetylaminoethyloxy)-para-phenylenediamine and their addition salts with an acid are particularly preferred.

Mention may be made, among bisphenylalkylenediamines, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis-(β-hydroxyethyl)-N,N'-bis(4-aminophenyl)tetramethylenediamine, N,N'-bis(4-methylaminophenyl) tetramethylene-diamine, N,N'-bis(ethyl)-N,N'-bis(4'-amino-3'-methyl-phenyl) ethylenediamine, 1,8-bis(2,5-diaminophenoxy)-3,6-dioxaoctane and their addition salts.

Mention may be made, among para-aminophenols, by way of example, of para-aminophenol, 4-amino-3-methylphenol, 4-amino-3-fluorophenol, 4-amino-3-chlorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-2-(aminomethyl)phenol, 4-amino-2-((β-hydroxyethyl)aminomethyl)phenol, 4-amino-2-fluorophenol and their addition salts with an acid.

Mention may be made, among ortho-aminophenols, by way of example, of 2-aminophenol, 2-amino-5-methylphenol, 2-amino-6-methylphenol, 5-acetamido-2-aminophenol and their addition salts.

Mention may be made, among heterocyclic bases, by way of example, of pyridine derivatives, pyrimidine derivatives and pyrazole derivatives.

Mention may be made, among pyridine derivatives, of the compounds described, for example, in Patents GB 1 026 978 and GB 1 153 196, such as 2,5-diaminopyridine, 2-[(4-methoxyphenyl)amino]-3-aminopyridine, 3,4-diaminopyridine and their addition salts.

Other pyridine oxidation bases of use in the present invention are the 3-aminopyrazolo[1,5-a]pyridine oxidation bases or their addition salts described, for example, in Patent Application FR 2 801 308. Mention may be made, by way of example, of pyrazolo[1,5-a]pyridin-3-ylamine; 2-(acetylamino)-pyrazolo[1,5-a]pyridin-3-ylamine; 2-(morpholin-4-yl)-pyrazolo[1,5-a]pyridin-3-ylamine; 3-aminopyrazolo-[1,5-a]pyridine-2-carboxylic acid; 2-methoxypyrazolo-[1,5-a]pyridin-3-ylamine; (3-aminopyrazolo[1,5-a]-pyridin-7-yl)methanol; 2-(3-aminopyrazolo[1,5-a]-pyridin-5-yl)ethanol; 2-(3-aminopyrazolo[1,5-a]pyridin-7-yl)ethanol; (3-aminopyrazolo[1,5-a]pyridin-2-yl)methanol; 3,6-diaminopyrazolo[1,5-a]pyridine; 3,4-diaminopyrazolo[1,5-a]pyridine; pyrazolo[1,5-a]-pyridine-3,7-diamine; 7-(morpholin-4-yl)pyrazolo-[1,5-a]pyridin-3-ylamine; pyrazolo[1,5-a]pyridine-3,5-diamine; 5-(morpholin-4-yl)pyrazolo[1,5-a]pyridin-3-ylamine; 2-[(3-aminopyrazolo[1,5-a]pyridin-5-yl)(2-hydroxyethyl)amino]ethanol; 2-[(3-amino-pyrazolo[1,5-a]pyridin-7-yl) (2-hydroxyethyl)amino]-ethanol; 3-aminopyrazolo[1,5-a]pyridin-5-ol; 3-amino-pyrazolo[1,5-a]pyridin-4-ol; 3-aminopyrazolo[1,5-a]-pyridin-6-ol; 3-aminopyrazolo[1,5-a]pyridin-7-ol; and their addition salts.

Mention may be made, among pyrimidine derivatives, of the compounds described, for example, in Patents DE 2 359 399; JP 88-169571; JP 05-63124; EP 0 770 375 or Patent Application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and their addition salts and their tautomeric forms, when a tautomeric equilibrium exists.

Mention may be made, among pyrazole derivatives, of the compounds described in Patents DE 3 843 892 and DE 4 133 957 and Patent Applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-(tert-butyl)-1-methylpyrazole, 4,5-diamino-1-(tert-butyl)-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-(hydroxymethyl)pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triamino-pyrazole, 1-methyl-3,4,5-triaminopyrazole, 3,5-diamino-1-methyl-4-(methylamino) pyrazole, 3,5-diamino-4-(β-hydroxyethyl)amino-1-methylpyrazole and their addition salts. Use may also be made of 4,5-diamino-1-(β-methoxyethyl)pyrazole.

The oxidation base or bases present in the composition of the invention are generally present in an amount ranging from 0.001 to 20% by weight approximately of the total weight of the dyeing composition, preferably ranging from 0.005 to 6%.

If the composition comprises at least one oxidation base, the composition according to the invention preferably comprises one or more couplers conventionally used for the dyeing of keratinous fibres. Mention may in particular be made, among these couplers, of meta-phenylenediamines, meta-aminophenols, meta-diphenols, naphthalene couplers or heterocyclic couplers and their addition salts.

Mention may be made, by way of example, of 1,3-dihydroxybenzene, 1,3-dihydroxy-2-methylbenzene, 4-chloro-1,3-dihydroxybenzene, 2,4-diamino-1-(β-hydroxyethyloxy) benzene, 2-amino-4-(β-hydroxyethyl-amino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino) toluene, 6-hydroxyindoline, 2,6-dihydroxy-4-methylpyridine, 1H-3-methylpyrazole-5-one, 1-phenyl-3-methylpyrazole-5-one, 2,6-dimethylpyrazolo[1,5-b][1,2,4]triazole, 2,6-dimethyl[3,2-c][1,2,4]triazole, 6-methylpyrazole-[1,5-a]benzimidazole, their addition salts with an acid and their mixtures.

In the composition of the present invention, the coupler or couplers are generally present in an amount ranging from 0.001 to 20% by weight approximately of the total weight of the dyeing composition, preferably ranging from 0.005 to 6%.

Generally, the addition salts of the oxidation bases and couplers which can be used in the context of the invention are chosen in particular from the addition salts with an acid, such as hydrochlorides, hydrobromides, sulphates, citrates, succinates, tartrates, lactates, tosylates, benzenesulphonates, phosphates and acetates.

According to a first embodiment of the invention, when the composition is in the form of a paste, the oxidation dye or dyes, that is to say the oxidation base or bases optionally in combination with one or more couplers, are chosen from the compounds listed above.

According to a second embodiment of the invention, when the composition is in the pulverulent form, the oxidation dye or dyes, that is to say the oxidation base or bases optionally in combination with one or more couplers, are chosen from benzene compounds. The term "benzene compound" is understood to mean, within the meaning of the invention, any compound comprising, in its structure, as ring, only one or more unfused benzene rings.

Thus, the composition according to the invention comprises either one or more benzene oxidation bases, or one or more benzene couplers, or their combinations. It should be noted that it is not ruled out for the composition to comprise, in addition to the above-mentioned benzene oxidation dye or dyes, one or more nonbenzene oxidation bases, one or more nonbenzene couplers or their combinations.

By way of example, the benzene oxidation bases are chosen from para-phenylenediamines, bisphenylalkylenediamines, para-aminophenols, ortho-aminophenols and their addition salts.

Mention may in particular be made, among benzene couplers, of meta-phenylenediamines, meta-aminophenols, meta-diphenols and their addition salts.

According to an alternative form of this embodiment, the composition can also comprise one or more additional nonbenzene oxidation bases advantageously chosen from heterocyclic bases. Mention may be made, among suitable heterocyclic bases, by way of example, of pyridine derivatives, pyrimidine derivatives and pyrazole derivatives.

According to another alternative form of this embodiment, the composition can also comprise one or more additional nonbenzene couplers. More particularly, the latter are chosen from naphthalene or heterocyclic couplers.

In all these cases, reference may be made to the lists given previously relating to these compounds In accordance with an advantageous embodiment of the invention, the composition is devoid of direct dye.

The composition additionally comprises one or more complexes of hydrogen peroxide and of a polymer comprising, as monomer, at least one vinyl heterocyclic monomer.

More particularly, the vinyl heterocyclic monomer is chosen from monomers comprising a 4- to 6-membered heterocycle, optionally fused to a benzene ring, which comprises from 1 to 4 identical or different intracyclic heteroatoms; the number of intracyclic heteroatoms being less than that of the ring members of the heterocycle. Preferably, the number of intracyclic heteroatoms is 1 or 2.

More particularly, the heteroatom or heteroatoms is/are chosen from sulphur, oxygen or nitrogen, preferably from nitrogen and oxygen. In accordance with an even more advantageous embodiment of the invention, the monomer comprises at least one intracyclic nitrogen atom.

The vinyl heterocycle can optionally be substituted by one or more $C_1$-$C_4$, preferably $C_1$-$C_2$, alkyl groups.

Preferably, the heterocyclic monomer is chosen from N-vinyl monomers.

Mention may be made, among the monomers which can be envisaged, of the following monomers, which are optionally substituted: N-vinylpyrrolidone, vinylcaprolactam, N-vinylpiperidone, N-vinyl-3-morpholine, N-vinyl-4-oxazolinone, 2-vinylpyridine, 4-vinyl-pyridine, 2-vinylquinoline, 1-vinylimidazole or 1-vinylcarbazole. Preferably, the monomer is optionally substituted N-vinylpyrrolidine.

In accordance with a particularly advantageous embodiment of the invention, the polymer is a homopolymer.

However, the use of a copolymer is not ruled out. In such a case, the comonomer or comonomers is/are chosen from vinyl acetate, (meth)acrylic acids, (meth)acrylamides, or $C_1$-$C_4$ alkyl esters of (meth)acrylic acid, which may or may not be substituted.

The polymer involved in this complex can furthermore be soluble or insoluble in water. Preferably, it is soluble in water. It can exert variable average molecular weights, preferably between $10^3$ and $3\times10^6$ g/mol, preferably between $10^3$ and $2\times10^6$ g/mol. It is also possible to employ blends of such polymers.

Advantageously, the said complex comprises from 10 to 30% by weight of hydrogen peroxide, more particularly from 13 to 25% by weight and preferably from 18 to 22% by weight, with respect to the total weight of the complex.

According to a yet more advantageous alternative form of the invention, in this complex, the molar ratio of the vinyl heterocyclic monomer or monomers to the hydrogen peroxide ranges from 0.5 to 2, preferably from 0.5 to 1.

This complex is advantageously provided in the form of a substantially anhydrous powder, that is to say comprising less than 5% by weight of water.

Complexes of this type are described in particular in U.S. Pat. No. 5,008,106, U.S. Pat. No. 5,077,047, EP 832 846, EP 714 919, DE 4344131 and DE 19545380.

Mention may be made, as examples of complexes, for example, of the products of the Peroxydone K-30, Peroxydone KS90 or Peroxydone XL-10 type and also the complexes formed with hydrogen peroxide and one of the following polymers of Plasdone K-17, Plasdone K-25, Plasdone K-29/32, Plasdone K-90, Polyplasdone INF-10, Polyplasdone XL-10, Polyplasdone XL, Plasdone S-630, Styleze 2000 terpolymer or Ganex copolymers series type, which are sold by ISP.

The anhydrous composition according to the invention advantageously comprises from 0.1 to 50% by weight of polymer complex comprising, as monomer, at least one vinyl heterocyclic monomer and hydrogen peroxide, preferably from 1 to 30% by weight, with respect to the total weight of the composition.

The anhydrous composition additionally comprises one or more alkaline agents.

The alkaline agent or agents is/are chosen more particularly from ammonia, silicates, such as silicates and metasilicates, phosphates, hydrogenphosphates, carbonates or hydrogencarbonates of alkali metals or alkaline earth metals, such as lithium, sodium, potassium, magnesium, calcium or barium, and their mixtures.

Preferably, the alkaline agent or agents is/are chosen from alkali metal silicates or carbonates, and their mixtures.

The concentration of alkaline agents advantageously represents from 0.01 to 40% by weight and preferably from 0.1 to 30% by weight of the total weight of the composition.

Preferably, the composition according to the invention also comprises one or more ammonium salts, such as ammonium chloride, ammonium sulphate, ammonium phosphate or ammonium nitrate.

In accordance with an even more advantageous embodiment of the invention, the ammonium salt is ammonium chloride.

The concentration of ammonium salt(s), if they are present, is advantageously between 0.01 and 40% by weight, with respect to the total weight of the composition, preferably from 0.1 to 30% by weight, with respect to the total weight of the composition.

In the case where the composition is provided in the form of a paste, the composition according to the invention additionally comprises one or more inert organic liquids.

The term "inert liquid" is understood to mean, within the meaning of the present invention, any compound capable of flowing at ambient temperature, generally between 15° C. and 40° C., and at atmospheric pressure under the action of its own weight.

Inert means that the liquid does not react, at least under the storage conditions, with the ingredients of the composition.

Mention may be made, as examples of inert liquid, of polydecenes of formula $C_{10n}H_{[(20n)+2]}$ in which n varies from 3 to 9 and preferably from 3 to 7, esters and in particular esters of fatty alcohols or of fatty acids, esters or diesters of sugars and of $C_{12}$-$C_{24}$ fatty acids, or cyclic esters, cyclic ethers, silicone oils, mineral oils, vegetable oils or animal oils, or their mixtures.

The compounds of formula $C_{10n}H_{[(20n)+2]}$ with n varying from 3 to 9 correspond to the term "polydecene" of the CTFA dictionary, 7$^{th}$ edition, 1997, of the Cosmetic, Toiletry and Fragrance Association, USA, and to the same INCI term in the USA and in Europe. These are hydrogenation products of poly-1-decenes.

Among these compounds, preference is given, according to the invention, to those for which, in the formula, n varies from 3 to 7.

Mention may be made, as example, of the product sold under the name Silkflo® 366 NF Polydecene by Amoco Chemical or those sold under the name Nexbase® 2002 FG, 2004 FG, 2006 FG and 2008 FG by Fortum.

As regards the esters, mention may be made, as example, of:

esters of saturated, linear or branched, lower $C_3$-$C_6$ monoalcohols with monofunctional $C_{12}$-$C_{24}$ fatty acids, it being possible for the latter to be saturated or unsaturated and linear or branched, and chosen in particular from oleates, laurates, palmitates, myristates, behenates, cocoates, stearates, linoleates, linolenates, caprates, arachidonates, or their mixtures, such as, in particular, oleopalmitates, oleostearates or palmitostearates. Preference is more particularly given, among these esters, to the use of isopropylpalmitate, isopropylmyristate, octyldodecylstearate and isononyl isononanoate.

esters of linear or branched $C_3$-$C_8$ monoalcohols with bifunctional $C_8$-$C_{24}$ fatty acids, it being possible for the latter to be saturated or unsaturated and linear or branched, such as, for example, the diisopropyl ester of sebacic acid, also known as diisopropyl sebacate, esters of linear or branched $C_3$-$C_8$ monoalcohols with bifunctional $C_2$-$C_8$ acids, it being possible for the latter to be saturated or unsaturated and linear or branched, such as, for example, dioctyl adipate and dicaprylyl maleate, the ester of a trifunctional acid, such as triethyl citrate.

As regards the esters and diesters of sugars and of $C_{12}$-$C_{24}$ fatty acids, the term "sugar" is understood to mean compounds which have several alcohol functional groups, with or without an aldehyde or ketone functional group, and which comprise at least 4 carbon atoms. These sugars can be monosaccharides, oligo-saccharides or polysaccharides.

Mention may be made, as sugars which can be used according to the invention, for example, of sucrose, glucose, galactose, ribose, fucose, maltose, fructose, mannose, arabinose, xylose, lactose and their derivatives, in particular alkylated derivatives, such as methylated derivatives, for example methylglucose.

The esters of sugars and of fatty acids which can be used according to the invention can be chosen in particular from the group consisting of the esters or mixtures of esters of sugars described above and of $C_{12}$-$C_{24}$ fatty acids which are saturated or unsaturated and linear or branched.

The esters can be chosen from mono-, di-, tri- and tetraesters, polyesters and their mixtures.

These esters can, for example, be chosen from oleates, laurates, palmitates, myristates, behenates, cocoates, stearates, linoleates, linolenates, caprates, arachidonates or their mixtures, such as, in particular, oleopalmitate, oleostearate or palmitostearate mixed esters.

More particularly, preference is given to the use of mono- and diesters, in particular mono- or dioleates, -stearates, -behenates, -oleopalmitates, -linoleates, -linolenates or -oleostearates, of sucrose, of glucose or of methylglucose.

Mention may be made, as example, of the product sold under the name Glucate® DO by Amerchol, which is a methylglucose dioleate.

Mention may also be made, as examples of esters or mixtures of esters of sugars and of fatty acids, of:

the products sold under the names F160, F140, F110, F90, F70 and SL40 by Crodesta, respectively denoting sucrose palmitostearate formed of 73% of monoester and 27% of di- and triester, of 61% of monoester and 39% of di-, tri- and tetraester, of 52% of monoester and 48% of di-, tri- and tetraester, of 45% of monoester and 55% of di-, tri- and tetraester, and of 39% of monoester and 61% of di-, tri- and tetraester, and sucrose monolaurate;

the products sold under the name Ryoto Sugar Esters, for example reference B370 and corresponding to sucrose behenate formed of 20% of monoester and 80% of di-, tri- and polyester;

the sucrose mono- and dipalmitostearate sold by Goldschmidt under the name Tegosoft® PSE.

As regards the cyclic ethers and cyclic esters, γ-butyrolactone, dimethyl isosorbide or diisopropyl isosorbide are suitable in particular.

Silicone oils can also be employed as inert organic liquid.

More particularly, suitable silicone oils are liquid silicone fluids with a viscosity of less than or equal to 10 000 mPa·s at 25° C., the viscosity of the Silicones being measured according to Standard ASTM 445 Appendix C.

Silicone oils are defined in more detail in the work by Walter Noll, "Chemistry and Technology of Silicones", 1968, Academic Press.

Mention may in particular be made, among silicone oils which can be used according to the invention, of the silicone oils sold under the names DC 200 Fluid-5 mPa·s, DC 200 Fluid-20 mPa·s, DC 200 Fluid-350 mPa·s, DC 200 Fluid-1000 mPa·s, DC 200 Fluid-10 000 mPa·s, DC 8566 Amino Fluid and DC 245 Fluid by Dow Corning.

Mineral oils can also be used as inert organic liquid, such as, for example, liquid paraffin or liquid petrolatum.

Vegetable oils may also be suitable, in particular avocado oil, olive oil, jojoba liquid wax or camellia oil, as well as animal oils, such as lanolin.

Use may also be made of nonpolar solvents, such as, in particular, nonpolar dicapryl derivatives and more particularly dicapryl carbonate or dicapryl ether.

Preferably, the inert organic liquid is chosen from polydecenes of formula $C_{10n}H_{[(20n)+2]}$ in which n varies from 3 to 9 and preferably from 3 to 7, esters of fatty alcohols or of fatty acids, liquid petrolatum, liquid paraffin and their mixtures.

The content of inert organic liquid(s) varies in the composition advantageously from 10 to 50% by weight, with respect to the weight of the composition, and preferably from 20 to 50% by weight, with respect to the weight of the composition.

The composition can optionally comprise at least one peroxygenated salt.

The peroxygenated salts are more particularly chosen from persulphates, perborates and percarbonates of alkali metals or alkaline earth metals, such as sodium, potassium or magnesium.

According to a preferred alternative form of the invention, the composition comprises, as peroxygenated salts, persulphates and, among these, mainly sodium persulphate and potassium persulphate.

Usually, the content of peroxygenated salt(s), if it is present, represents from 1 to 70% by weight, more particularly from 10 to 70% by weight and preferably from 20 to 60% by weight, with respect to the total weight of the said composition.

The composition according to the invention can additionally comprise one or more thickening polymers.

Advantageously, the thickening polymers are chosen from the following polymers:

(i) nonionic amphiphilic polymers comprising at least one fatty chain and at least one hydrophilic chain;

(ii) anionic amphiphilic polymers comprising at least one hydrophilic unit and at least one unit comprising a fatty chain;

(iii) crosslinked acrylic acid homopolymers;

(iv) crosslinked 2-acrylamido-2-methylpropanesulphonic acid homopolymers and their crosslinked copolymers of acrylamide, partially or completely neutralized;

(v) homopolymers of ammonium acrylate or copolymers of ammonium acrylate and of acrylamide;

(vi) homopolymers of dimethylaminoethyl methacrylate quaternized with methylchloride or copolymers of dimethylaminoethyl methacrylate quaternized with methylchloride and of acrylamide;

(vii) polysaccharides;

(viii) scleroglucan gums (biopolysaccharide of microbial origin);

(ix) gums resulting from plant exudates, such as gum Arabic, ghatti gum, karaya gum and gum tragacanth;

(x) celluloses and derivatives.

It should be noted that, in the case of the present invention, the thickening polymers have a role with regard to the viscosity of the ready-for-use composition, that is to say of the composition resulting from the mixing of the anhydrous composition according to the invention with at least water.

According to the invention, amphiphilic polymers are more particularly hydrophilic polymers capable, in the medium of the composition and more particularly an aqueous medium, of combining reversibly with one another or with other molecules.

Their chemical structure comprises more particularly at least one hydrophilic region and at least one hydrophobic region. The term "hydrophobic group" is understood to mean a radical or polymer having a saturated or unsaturated and linear or branched hydrocarbon chain comprising at least 8 carbon atoms, preferably at least 10 carbon atoms, preferably from 10 to 30 carbon atoms, in particular from 12 to 30 carbon atoms and more preferably from 18 to 30 carbon atoms. Preferably, the hydrocarbon group originates from a monofunctional compound. By way of example, the hydrophobic group can result from a fatty alcohol, such as stearyl alcohol, dodecyl alcohol or decyl alcohol. It can also denote a hydrocarbon polymer, such as, for example, polybutadiene.

The nonionic amphiphilic thickening polymers comprising at least one fatty chain and at least one hydrophilic unit are preferably chosen from:

(1) celluloses modified by groups comprising at least one fatty chain;

mention may be made, by way of example, of:
  hydroxyethylcelluloses modified by groups comprising at least one fatty chain, such as alkyl, arylalkyl or alkylaryl groups, or their mixtures, and in which the alkyl groups are preferably $C_8$-$C_{22}$ alkyl groups, such as the product Natrosol Plus Grade 330 CS($C_{1-6}$ alkyl) sold by Aqualon or the product Bermacoll EHM 100 sold by Berol Nobel,
  those modified by alkylphenol polyalkylene glycol ether groups, such as the product Amercell Polymer HM-1500 (nonylphenol polyethylene glycol (15) ether) sold by Amerchol.

(2) hydroxypropyl guars modified by groups comprising at least one fatty chain, such as the product Esaflor HM 22 ($C_{2-2}$ alkyl chain) sold by Lamberti or the products Miracare XC95-3 ($C_{1-4}$ alkyl chain) and RE205-1 ($C_{20}$ alkyl chain) sold by Rhône-Poulenc.

(3) polyether urethanes comprising at least one fatty chain, such as $C_8$-$C_{30}$ alkyl or alkenyl groups, for example the products Dapral T 210 and Dapral T 212 sold by Akzo.

(4) copolymers of vinylpyrrolidone and of hydrophobic monomers comprising a fatty chain;

mention may be made, by way of example, of;
the products Antaron V216 or Ganex V216 (vinylpyrrolidone/hexadecane copolymer) sold by I.S.P.,
the products Antaron V220 or Ganex V220 (vinyl-pyrrolidine/eicosene copolymer) sold by I.S.P.

(5) copolymers of $C_1$-$C_6$ alkyl methacrylates or acrylates and of amphiphilic monomers comprising at least one fatty chain, such as, for example, the methyl methacrylate/oxyethylenated stearyl acrylate copolymer sold by Goldschmidt under the name Antil 208.

(6) copolymers of hydrophilic methacrylates or acrylates and of hydrophobic monomers comprising at least one fatty chain, such as, for example, the polyethylene glycol methacrylate/lauryl methacrylate copolymer.

Mention may be made, among anionic amphiphilic polymers comprising at least one hydrophobic unit and at least one unit comprising a fatty chain, of those comprising at least one allyl ether unit comprising a fatty chain and at least one hydrophobic unit composed of an ethylenic unsaturated anionic monomer, more particularly of a vinyl carboxylic acid and very particularly of an acrylic acid, a methacrylic acid or their mixtures, the allyl ether unit comprising the fatty chain corresponding to the monomer of the following formula (1):

$$CH_2=CR'-CH_2-O-B_n-R \quad (1)$$

in which R' denotes H or $CH_3$, B denotes the ethyleneoxy radical, n is zero or denotes an integer ranging from 1 to 100 and R denotes a hydrocarbon radical chosen from alkyl, arylalkyl, aryl, alkylaryl or cycloalkyl radicals comprising from 8 to 30 carbon atoms, preferably from 10 to 24 carbon atoms and more particularly still from 12 to 18 carbon atoms.

A unit of the formula (1) which is more particularly preferred according to the present invention is a unit from which R' denotes H, n is equal to 10 and R denotes a stearyl ($C_{18}$) radical.

Anionic amphiphilic polymers of this type are described and prepared, according to an emulsion polymerization process, in Patent EP 0 216 479 B2.

Preference is particularly given according to the invention, among these anionic amphiphilic polymers, to the polymers formed from 20 to 60% by weight of acrylic acid and/or methacrylic acid, from 5 to 60% by weight of lower alkyl (meth)acrylates, from 2 to 50% by weight of allyl ether comprising a fatty chain of formula (1) and from 0 to 1% by weight of a crosslinking agent which is a well known copolymerizable polyethylenic unsaturated monomer, such as diallylphthalate, allyl (meth)acrylate, divinylbenzene, (polyethylene glycol dimethacrylate and methylenebisacrylamide.

Among the latter, preference is very particularly given to crosslinked terpolymers of methacrylic acid, of ethyl acrylate and of polyethylene glycol (10 EO) ether of stearyl alcohol (Steareth 10), in particular those sold by Allied Colloids under the names Salcare SC80 and Salcare SC90, which are 30% aqueous emulsions of a crosslinked terpolymer of methacrylic acid, of ethyl acrylate and of steareth-10 allyl ether (40/50/10).

The anionic amphiphilic polymers can also be chosen from those comprising at least one hydrophilic unit of olefinic unsaturated carboxylic acid type and at least one hydrophobic unit exclusively of alkyl ($C_{10}$-$C_{30}$) ester of unsaturated carboxylic acid type, used according to the invention, are preferably chosen from those for which the hydrophilic unit of olefinic unsaturated carboxylic acid type corresponds to the monomer of following formula (2):

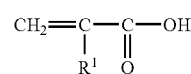

(2)

in which formula $R^1$ denotes H or $CH_3$ or $C_2H_5$ that is to say acrylic acid, methacrylic acid or ethacrylic acid units, and for which the hydrophobic unit of alkyl ($C_{10}$-$C_{30}$) ester of unsaturated carboxylic acid type corresponds to the monomer of following formula (3):

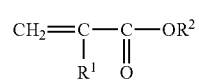

(3)

in which formula $R^1$ denotes H or $CH_3$ or $C_2H_5$ (that is to say, acrylate, methacrylate or ethacrylate units) and preferably H (acrylate units) or $CH_3$ (methacrylate units), $R^2$ denoting a $C_{10}$-$C_{30}$ and preferably $C_{12}$-$C_{22}$ alkyl radical.

Alkyl ($C_{10}$-$C_{30}$) esters of unsaturated carboxylic acids comprise, for example, lauryl acrylate, stearyl acrylate, decyl acrylate, isodecyl acrylate, dodecyl acrylate, and the corresponding methacrylates, lauryl methacrylate, stearyl methacrylate, decyl methacrylate, isodecyl methacrylate and dodecyl methacrylate.

Anionic amphiphilic polymers of this type are, for example, described and prepared according to Patents U.S. Pat. Nos. 3,915,921 and 4,509,949.

The anionic amphiphilic polymers which can be used in the context of the present invention can more particularly denote polymers formed from a mixture of monomers comprising:

(i) essentially acrylic acid, an ester of following formula (3):

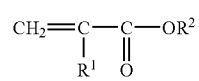

(3)

in which $R^1$ denotes H or $CH_3$, $R^2$ denoting an alkyl radical having from 12 to 22 carbon atoms, and a crosslinking agent, such as, for example, those composed of 95 to 60% by weight of acrylic acid (hydrophilic unit), 4 to 40% by weight of $C_{10}$-$C_{30}$ alkyl acrylate (hydrophobic unit) and 0 to 6% by weight of crosslinking polymerizable monomer, or 98 to 96% by weight of acrylic acid (hydrophilic unit), 1 to 4% by weight of $C_{10}$-$C_{30}$ alkyl acrylate (hydrophobic unit) and 0.1 to 0.6% by weight of crosslinking polymerizable monomer, (ii) essentially acrylic acid and lauryl methacrylate, such as that formed from 66% by weight of acrylic acid and 34% by weight of lauryl methacrylate.

The said crosslinking agent is a monomer comprising a $CH_2=CH<$ group with at least one other polymerizable group, the unsaturated bonds of which are nonconjugated with respect to one another. Mention may in particular be made of polyallyl ethers, such as in particular polyallyl sucrose and polyallyl pentaerythritol.

Preference is very particularly given according to the present invention, among the said polymers above, to the products sold by Goodrich under the trade names Pemulen TR1, Pemulen TR2 and Carbopol 1382, more preferably still Pemulen TR1, and the product sold by S.E.P.P.I.C. under the name Coatex SX.

Mention may be made, among crosslinked acrylic acid homopolymers which can be used in the context of the present invention, of those crosslinked by an allyl ether of an alcohol of the sugar series, such as, for example, the products sold under the names Carbopol 980, Carbopol 981, Carbopol 954, Carbopol 2984 and Carbopol 5984 by Goodrich or the products sold under the names Synthalen M and Synthalen K by 3 VSA.

Mention may be made, among crosslinked homopolymers of 2-acrylamido-2-methylpropanesulphonic acid, of those described in Application EP-A-0 815 828 (forming an integral part of the content of the description). Mention may in particular be made, among crosslinked copolymers of 2-acrylamido-2-methylpropanesulphonic acid and of acrylamide which are partially or completely neutralized (with a base, such as sodium hydroxide, potassium hydroxide or an amine), of the product described in Example 1 of the document EP-A-503 853 (forming an integral part of the content of the description).

Mention may be made, among homopolymers of ammonium acrylate, of the product sold under the name Microsap PAS 5193 by Hoechst. Mention may be made, among copolymers of ammonium acrylate and of acrylamide, of the product sold under the name Bozepol C Nouveau [New] or the product PAS 5193 which are sold by Hoechst (they are described and prepared in the documents FR 2 416 723, U.S. Pat. No. 2,798,053 and U.S. Pat. No. 2,923,692).

Mention may be made, among homopolymers of dimethylaminoethyl methacrylate quaternized with methyl-chloride, of the products sold under the names Salcare 95 and Salcare 96 by Allied Colloids. Mention may be made, among copolymers of dimethylaminoethyl methacrylate quaternized with methylchloride and with acrylamide, of the product Salcare SC92 sold by Allied Colloids or the product PAS 5194 sold by Hoechst (they are described and prepared in the document EP-A-395 282).

Mention may be made, among polysaccharides, of anionic polysaccharides, such as pectins or carrageenans, cationic polysaccharides, such as chitosan, or nonionic polysaccharides, such as unmodified guar gums.

More particularly, unmodified nonionic guar gums are, for example, the products sold under the name Vidogum GH 175 by Unipectine and under the name Jaguar C by Meyhall.

The nonionic gums which can be used according to the invention are preferably modified with $C_1$-$C_6$ hydroxy-alkyl groups.

Mention may be made, among hydroxyalkyl groups, by way of example, of the hydroxymethyl, hydroxyethyl, hydroxypropyl and hydroxybutyl groups.

These guar gums are well known from the state of the art and can, for example, be prepared by reacting corresponding alkene oxides, such as, for example, propylene oxides, with the guar gum, so as to obtain a guar gum modified with hydroxypropyl groups.

The degree of hydroxyalkylation, which corresponds to the number of alkylene oxide molecules consumed by the number of free hydroxyl functional groups present on the guar gum, preferably varies from 0.4 to 1.2.

Such nonionic guar gums optionally modified with hydroxyalkyl groups are, for example, sold under the trade names Jaguar HP8, Jaguar HP60, Jaguar HP120, Jaguar DC 293 and Jaguar HP 105 by Rhône-Poulenc (Meyhall) or under the name Galactasol 4H4FD2 by Aqualon.

Scleroglucan gum (biopolysaccharide of microbial origin) and gums resulting from plant exudates, such as gum Arabic, ghatti gum, karaya gum and gum tragacanth, are well known to a person skilled in the art and are described in particular in the work by Robert L. Davidson entitled "Handbook of Water-soluble Gums and Resins", published by McGraw Hill Book Company (1980).

As regards the celluloses and derivatives, mention may in particular be made of nonionic cellulose ethers, such as hydroxyalkylcelluloses ($C_2$-$C_3$ alkyl), for example with Natrosol 250HHR, cationic celluloses, such as Polyquaternium-10 (CTFA name), for example with the product Ucare Polymer FR400, or Polyquaternium-4 (CTFA name), or anionic celluloses, with carboxyalkyl-cellulose ($C_1$-$C_2$ alkyl).

The thickening polymers are preferably used in an amount which can vary from 0.01 to 15% by weight, with respect to the weight of the composition, and preferably from 0.1 to 10% by weight, with respect to the weight of the composition.

The composition according to the invention can comprise one or more surface-active agents.

The term "surface-active agent" is understood to mean, within the meaning of the present invention, an agent comprising at least one hydrophilic group and at least one lipophilic group in its structure, and which is preferably capable of reducing the surface tension of water, and comprising, in its structure, as possible repeat units, only alkylene oxide units and/or sugar units and/or siloxane units. Preferably, the lipophilic group is a fatty chain comprising from 8 to 30 carbon atoms.

This surface-active agent can be chosen from anionic, amphoteric, nonionic or cationic surface-active agents or their mixtures.

The surfactants which are suitable for the implementation of the present invention are in particular as follows;

(i) Anionic Surfactant(s):

Mention may in particular be made, as example of anionic surfactants which can be used, alone or as mixtures, in the context of the present invention, of the salts (in particular alkali metal salts, in particular sodium salts, ammonium salts, amine salts, aminoalcohol salts or alkaline earth metal salts, such as the magnesium salt) of the following compounds:

alkyl sulphates, alkyl ether sulphates, alkylamido ether sulphates, alkylarylpolyether sulphates or monoglyceride sulphates;

alkylsulphonates, alkylamidesulphonates, alkylarylsulphonates, α-olefinsulphonates or paraffin sulphonates;

alkyl phosphates or alkyl ether phosphates;

alkyl sulphosuccinates, alkyl ether sulpho-succinates, alkylamidesulphosuccinates or alkyl sulphosuccinamates;

alkyl sulphoacetates;

acylsarcosinates, acylisethionates and N-acyl-taurates;

salts of fatty acids, such as oleic acid, ricinoleic acid, palmitic acid, stearic acid, coconut oil acid or hydrogenated coconut oil acid;

salts of alkyl-D-galactosideuronic acids;

acyllactylates;

salts of polyoxyalkylenated alkyl ether carboxylic acids, of polyoxyalkylenated alkylaryl ether carboxylic acids or of polyoxyalkylenated alkylamido ether carboxylic acids, in particular those comprising from 2 to 50 ethylene oxide groups;

and their mixtures.

It should be noted that the alkyl or acyl radical of these various compounds advantageously comprises from 6 to 24 carbon atoms, preferably from 8 to 24 carbon atoms, and the aryl radical preferably denotes a phenyl or benzyl group.

(ii) Nonionic Surfactant(s):

The nonionic surface-active agents are themselves also compounds well known per se (see in particular in this regard "Handbook of Surfactants" by M R Porter, published by Blackie & Son (Glasgow and London), 1991, pp. 116-178).

They can in particular be chosen from:
polyethoxylated, polypropoxylated or polyglycerolated fatty alcohols, polyethoxylated, polypropoxylated or polyglycerolated α-diols or polyethoxylated, polypropoxylated or polyglycerolated alkylphenols, it being possible for the number of ethylene oxide or propylene oxide groups to range in particular from 2 to 50 and it being possible for the number of glycerol groups to range in particular from 2 to 30;

copolymers of ethylene oxide and of propylene oxide or condensates of ethylene oxide and of propylene oxide with fatty alcohols;

polyethoxylated fatty amides preferably having from 2 to 30 mol of ethylene oxide or polyglycerolated fatty amides more particularly comprising, on average, 1 to 5 glycerol groups and in particular 1.5 to 4;

oxyethylenated sorbitan fatty acid esters having more particularly from 2 to 30 mol of ethylene oxide, sucrose fatty acid esters or polyethylene glycol fatty acid esters;

alkylpolyglycosides;

N-alkylglucamine derivatives or amine oxides, such as alkylamine oxides or N-acylaminopropyl-morpholine oxide;

and their mixtures.

More particularly, in the above compounds, the fatty chain or the alkyl chain or the acyl group comprises, for example, from 8 to 30 carbon atoms.

It should be noted that alkylpolyglycosides constitute nonionic surfactants falling particularly well within the context of the present invention.

(iii) Amphoteric Surfactant(s):

The amphoteric surface-active agents can in particular be:
aliphatic secondary or tertiary amine derivatives in which the aliphatic radical is a linear or branched chain comprising from 8 to 24 carbon atoms and comprising at least one water-solubilizing anionic group (for example, carboxylate, sulphonate, sulphate, phosphate or phosphonate groups);

alkyl betaines, alkyl sulphobetaines, alkyl is amido ($C_1$-$C_6$)alkyl betaines or alkyl amido-($C_1$-$C_6$)alkyl sulphobetaines, with an alkyl chain comprising from 8 to 24 carbon atoms.

Mention may be made, among the amine derivatives, of the products sold under the Miranol names, such as described in Patents U.S. Pat. No. 2,528,378 and U.S. Pat. No. 2,781,354, and with the structures:

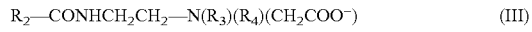

$$R_2\text{—CONHCH}_2\text{CH}_2\text{—N}(R_3)(R_4)(\text{CH}_2\text{COO}^-) \quad \text{(III)}$$

in which: $R_2$ denotes an alkyl radical derived from an acid $R_2$—COOH present in hydrolyzed coconut oil, or a heptyl, nonyl or undecyl radical, $R_3$ denotes a β-hydroxyethyl group and $R_4$ denotes a carboxymethyl group;

and

$$R_5\text{—CONHCH}_2\text{CH}_2\text{—N(B)(C)} \quad \text{(IV)}$$

in which:
B represents —$CH_2CH_2OX'$ and C represents —$(CH_2)_z$—Y', with z=1 or 2, X' denotes the —$CH_2CH_2$—COOH group or a hydrogen atom, Y' denotes —COOH or the —$CH_2$—CHOH—$SO_3H$ radical, $R_5$ denotes an alkyl radical of an acid $R_9$—COOH present in hydrolyzed coconut oil or in hydrolyzed linseed oil, or a linear or branched alkyl radical, in particular a $C_7$-$C_{17}$ alkyl radical, optionally comprising at least one ethylenic unsaturation.

These compounds are classified in the CTFA dictionary, 5th Edition, 1993, under the names Disodium Cocoamphodiacetate, Disodium Lauroamphodiacetate, Disodium Caprylamphodiacetate, Disodium Capryloamphodiacetate, Disodium Cocoamphodipropionate, Disodium Lauroamphodipropionate, Disodium Caprylamphodipropionate, Disodium Capryloamphodipropionate, Lauroamphodipropionic acid and Cocoamphodipropionic acid.

Mention may be made, by way of example, of the cocoamphodiacetate sold under the trade name Miranol C2M Concentrate by Rhodia Chimie.

(iv) Cationic Surfactant(s):

The cationic surfactants can be chosen from:

(A) quaternary ammonium salts of the following general formula (V):

(V)

in which $X^-$ is an anion chosen, for example, from the group of the halides (chloride, bromide or iodide) or ($C_2$-$C_6$) alkyl sulphates, more particularly methyl sulphate, of the phosphates, of the alkyl- or alkylarylsulphonates, and of the anions derived from an organic acid, such as acetate or lactate, and (1) the $R_1$ to $R_3$ radicals, which can be identical or different, represent a linear or branched aliphatic radical comprising from 1 to 4 carbon atoms or an aromatic radical, such as aryl or alkylaryl. The aliphatic radicals can comprise heteroatoms, such as, in particular, oxygen, nitrogen, sulphur or halogens. The aliphatic radicals are, for example, chosen from alkyl, alkoxy or alkylamide radicals, $R_4$ denotes a linear or branched alkyl radical comprising from 16 to 30 carbon atoms.

Preferably, the cationic surfactant is a behenyltrimethylammonium salt (for example chloride) and (2) the $R_1$ and $R_2$ radicals, which can be identical or different, represent a linear or branched aliphatic radical comprising from 1 to 4 carbon atoms or an aromatic radical, such as aryl or alkylaryl. The aliphatic radicals can comprise heteroatoms, such as, in particular, oxygen, nitrogen, sulphur or halogens. The aliphatic radicals are, for example, chosen from alkyl, alkoxy, alkylamide and hydroxyalkyl radicals comprising approximately from 1 to 4 carbon atoms;

$R_3$ and $R_4$, which are identical or different, denote a linear or branched alkyl radical comprising from 12 to 30 carbon atoms, said radical comprising at least one ester or amide functional group.

$R_3$ and $R_4$ are chosen in particular from $(C_{12}-C_{22})$alkylamido $(C_2-C_6)$alkyl or $(C_{12}-C_{22})$alkyl acetate radicals.

Preferably, the cationic surfactant is a stearamido-propyldimethyl(myristyl acetate)ammonium salt (for example chloride).

(B) imidazolinium quaternary ammonium salts, such as, for example, that of following formula (VI):

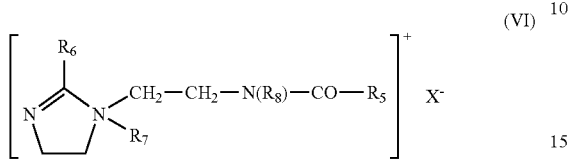

in which $R_5$ represents an alkenyl or alkyl radical comprising from 8 to 30 carbon atoms, for example derivatives of tallow fatty acids, $R_6$ represents a hydrogen atom, a $C_1-C_4$ alkyl radical or an alkenyl or alkyl radical comprising from 8 to 30 carbon atoms, $R_7$ represents a $C_1-C_4$ alkyl radical, $R_a$ represents a hydrogen atom or a $C_1-C_4$ alkyl radical and X is an anion chosen in particular from the group of the halides, phosphates, acetates, lactates, alkyl sulphates, or alkyl- or alkylarylsulphonates.

$R_5$ and $R_6$ preferably denote a mixture of alkenyl or alkyl radicals comprising from 12 to 21 carbon atoms, for example derivatives of tallow fatty acids, $R_7$ preferably denotes methyl and $R_8$ preferably denotes hydrogen. Such a product is, for example, Quaternium-27 (CTFA 1997) or Quaternium-83 (CTFA 1997), which are sold under the names "Rewoquat" W75, W90, W75PG or W75HPG by Witco, (C) diquaternary ammonium salts of formula (VII):

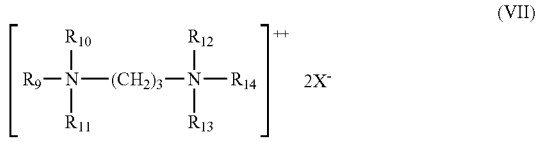

in which $R_9$ denotes an aliphatic radical comprising from 16 to 30 carbon atoms, $R_{10}$, $R_{11}$, $R_{12}$, $R_{13}$ and $R_{14}$, which are identical or different, are chosen from hydrogen or an alkyl radical comprising from 1 to 4 carbon atoms and X is an anion chosen in particular from the group of the halides, acetates, phosphates, nitrates and methyl sulphates.

Such diquaternary ammonium salts comprise in particular propanetallowediammonium dichloride, (D) quaternary ammonium salts comprising at least one ester functional group of following formula (VIII):

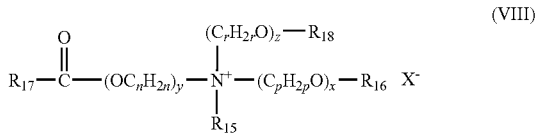

in which:
$R_{15}$ is chosen from $C_1-C_6$ alkyl radicals and $C_1-C_6$ hydroxyalkyl or dihydroxyalkyl radicals;

$R_{16}$ is chosen from:
  the $R_{19}$—CO— radical,
  saturated or unsaturated, linear or branched, $C_1-C_{22}$ hydrocarbon radicals $R_{20}$,
  the hydrogen atom,
$R_{18}$ is chosen from:
  the $R_{21}$—CO— radical,
  saturated or unsaturated, linear or branched, $C_1-C_6$ hydrocarbonaceous radicals $R_{22}$,
  the hydrogen atom,
$R_{17}$, $R_{19}$ and $R_{21}$ which are identical or different, are chosen from saturated or unsaturated, linear or branched, $C_7-C_{21}$, hydrocarbon radicals;
n, p and r, which are identical or different, are integers having values from 2 to 6;
y is an integer having a value from 1 to 10;
x and z, which are identical or different, are integers having values from 0 to 10;
$X^-$ is an organic or inorganic, simple or complex anion;
with the proviso that the sum x+y+z has a value from 1 to 15, that when x has a value of 0, then $R_{16}$ denotes $R_{20}$, and that when z has a value of 0, then $R_{18}$ denotes $R_{22}$;

or their mixtures.

Use is more particularly made of the ammonium salts of formula (VIII) in which:
$R_{15}$ denotes a methyl or ethyl radical,
x and y are equal to 1;
z is equal to 0 or 1;
n, p and r are equal to 2;
$R_{16}$ is chosen from:
  the $R_{19}$—CO— radical;
  methyl, ethyl or $C_{14}-C_{22}$ hydrocarbonaceous radicals;
  the hydrogen atom;
$R_{17}$, $R_{19}$ and $R_{21}$, which are identical or different, are chosen from saturated or unsaturated, linear or branched, $C_7-C_{21}$ hydrocarbon radicals;
$R_{18}$ is chosen from:
  the $R_{21}$—CO— radical;
  the hydrogen atom.

Such compounds are, for example, sold under the names Dehyquart by Cognis, Stepanquat by Stepan, Noxamium by Ceca or Rewoquat WE 18 by Rewo-Witco.

Preference is given, among quaternary ammonium salts, to behenyltrimethylammonium chloride, stearamidopropyl-dimethyltmyristyl acetate)ammonium chloride, sold under the name "Ceraphyl 70" by Van Dyk, or Quaternium-27 or Quaternium-83, which are sold by Witco.

The surfactant, when it is present, more particularly represents from 0.01% to 60% by weight, with respect to the total weight of the composition, preferably between 0.5% and 30% by weight and more preferably still between 1% and 20% by weight.

The anhydrous composition according to the invention can additionally comprise one or more cationic or amphoteric substantive polymers.

The substantive nature (that is to say, the ability to be deposited on the hair) of the polymers is conventionally determined by means of the test described by Richard J. Crawford, Journal of the Society of Cosmetic Chemists, 1980, 31(5), pages 273 to 278 (development by Acid Red 80 dye).

These substantive polymers are described in particular in the literature in Patent Application EP-A-0 557 203.

Mention may in particular be made, among substantive polymers of the homopolymer or copolymer of dimethyldiallylammonium halide type which can be used according to the invention, of:

polymers of diallyldimethylammonium chloride, such as polyquaternium-6 (Merquat 100 from Calgon);

copolymers of diallyldimethylammonium chloride and of acrylic acid, such as that with the proportions 80/20 by weight sold under the name Merquat 280 by Calgon;

the copolymers of dimethyldiallylammonium chloride and of acrylamide sold under the names Merquat 550 and Merquat S by Merck.

in particular those for which the molecular weight, determined by gel permeation is chromatography, is approximately 1200;

the polymers described and prepared in Patent U.S. Pat. Nos. 4,157,388, 4,390,689, 4,702,906 and 4,719,282, composed of repeat units corresponding to the following formula (III):

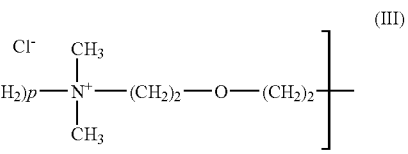

Mention may in particular be made, among substantive polymers of the polymer of methacryloyloxyethyltri-methylammonium halide type which can be used according to the invention, of the products which are named, in a CTFA dictionary (5$^{th}$ edition, 1993), "Polyquaternium 37", "Polyquaternium 32" and "Polyquaternium 35", which respectively correspond, as regards "Polyquaternium 37", to crosslinked poly(methacryloyloxyethyltrimethyl-ammonium chloride), as a 50% dispersion of mineral oil, sold under the name Salcare SC95 by Allied Colloids, as regards "Polyquaternium 32", to crosslinked copolymer of acrylamide and of methacryloyloxyethyltrimethyl-ammonium chloride (20/80 by weight), as a 50% dispersion in mineral oil, sold under the name Salcare. SC92 by Allied Colloids, and, as regards "Polyquaternium 35", to the methosulphate of the copolymer of methacryloyloxyethyltrimethylammonium and of methacryloyloxyethyldimethylacetylammonium, sold under the name Plex 7525L by Röhm GmbH.

The substantive polymers of the polyquaternary ammonium type which can be used according to the invention are as follows:

the polymers prepared and described in French Patent 2 270 846, composed of repeat units corresponding to the following formula (I):

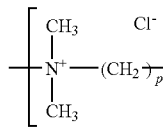

in particular those for which the molecular weight, determined by gel permeation chromatography, is between 9500 and 9900;

the polymers prepared and described in French Patent 2 270 846, composed of repeat units corresponding to the following formula (II):

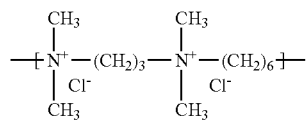

in which p denotes an integer varying from 1 to 6 approximately and D can be nonexistent or can represent a —(CH$_2$)$_r$—CO— group in which r denotes a number equal to 4 or to 7, in particular those for which the molecular weight is less than 100 000, preferably less than or equal to 50 000; such polymers are sold in particular by Miranol under the names "Mirapol A15", "Mirapol AD1", "Mirapol AZ1" and "Mirapol 175".

Mention may in particular be made, among vinylpyrrolidone polymers (PVPs) comprising cationic units which can be used in accordance with the invention, of:

a) vinylpyrrolidone polymers comprising dimethylaminoethyl methacrylate units; mention may be made, among these, of:

the small vinylpyrrolidone/dimethylaminoethyl methacrylate (20/80 by weight) copolymers sold under the trade name Copolymer 845 by I.S.P., vinylpyrrolidone/dimethylaminoethyl methacrylate copolymers quaternized with diethylsulphate, sold under the names Gafquat 734, 755, 755S and 755L by I.S.P., hydrophilic PVP/dimethylaminoethyl methacrylate/-polyurethanes, sold under the trade name Pecogel GC-310 by U.C.I.B. or also under the names Aquamere C 1031 and C 1511 by Blagden Chemicals, PVP/dimethylaminoethyl methacrylate/C$_8$ to C$_{16}$ olefins, quaternized or nonquaternized, sold under the names Ganex ACP 1050 to 1057, 1062 to 1069 and 1079 to 1086 by I.S.P., PVP/dimethylaminoethyl methacrylate/vinylcaprolactam, sold under the name Gaffix VC 713 by I.S.P., b) vinylpyrrolidone polymers comprising methacrylamidopropyltrimethylammonium (MAPTAC) units, among which may in particular be mentioned:

vinylpyrrolidone/MAPTAC copolymers, sold under the trade names Gafquat ACP 1011 and Gafquat HS 100 by I.S.P., c) vinylpyrrolidone polymers comprising methylvinyl-imidazolium units, among which may more particularly be mentioned:

PVP/methylvinylimidazolium chlorides, sold under the names Luviquat FC 370, FC 550, FC 905 and HM 552 by B.A.S.F., PVP/methylvinylimidazolium chloride/vinyl-imidazole, sold under the name Luviquat 8155 by B.A.S.F., PVP/methylvinylimidazolium methosulphate, sold under the name Luviquat MS 370 by B.A.S.F.

Mention may in particular be made, among cationic polysiloxanes, of those described in Patent Application EP-A-0 557 203, from page 8, line 48, to page 11, line 9, and more particularly still the products comprising "Amodimethicone" (CTFA name) of following formula (IV):

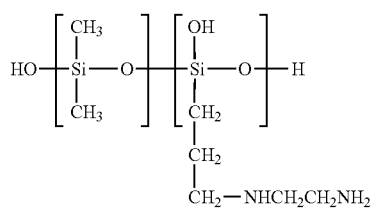

The concentration of cationic or amphoteric substantive polymer can vary between 0.01 and 10% approximately, with respect to the weight of the composition, and preferably between 0.1 and 5% by weight, with respect to the weight of the composition.

The composition according to the invention can also comprise various additives conventionally used in cosmetics.

The composition in accordance with the present invention can thus comprise inorganic or organic thickening agents, in particular fillers, such as clays; binders, such as vinylpyrrolidone; lubricating agents, such as polyolstearates or alkali metal or alkaline earth metal stearates; hydrophilic or hydrophobic silicas; pigments; matifying or opacifying agents, such as titanium oxide; antioxidants, such as erythorbic acid; reducing agents, such as sodium metabisulphite; penetrating agents; sequestering agents, such as ethylenediaminetetraacetic acid or its salts; moisture-absorbing agents, such as amorphous silicas or some crosslinked polyacrylates or polyacrylates modified with hydrophobic groups, such as, for example, the products Luquasorb 1010 from BASF or Polytrap 6603 adsorber from Amcol; buffers; dispersing agents; film-forming agents; preservatives; vitamins; fragrances; ceramides; or conditioning agents other than the substantive polymers mentioned above.

It should be noted that the composition can also comprise one or more coloured substances, the nature and/or the concentration of which do not make it possible to colour the keratinous fibres treated.

The composition in accordance with the invention can also comprise agents for controlling the release of oxygen, such as magnesium carbonate or oxide.

The additives and the agents for controlling the release of oxygen as defined above can be present in an amount of, for each of them, between 0.01 and 40% by weight, preferably between 0.1 and 30% by weight, with respect to the total weight of the composition.

Preferably, the anhydrous composition in the form of a paste is composed of a mixture of at least one powder and of at least one inert organic liquid.

In the case where the composition is in the pulverulent form, it can also comprise compounds which make possible agglomeration of water-soluble or water-insoluble and polymeric or nonpolymeric powder particles, such as, for example, polyvinyl alcohol or polyethylene oxide/polypropylene oxide copolymers (Pluronic®, Synperonic®).

Purely by way of illustration, their content generally does not exceed 5% by weight, with respect to the weight of the composition.

The anhydrous composition according to the invention in the form of a paste can advantageously be prepared by dispersing, using mechanical action, all the pulverulent compounds in the inert organic liquid, in which the other liquid compounds of the composition have been dispersed or mixed beforehand.

The paste can also be prepared by extrusion, by introducing the liquid and solid phases of the composition into an extruder and by then blending them at a temperature of less than 25° C. using a corotating twin-screw system composed of transportation and kneading elements.

The colouring method according to the invention consists in mixing the anhydrous composition which has just been described with an aqueous composition and in applying the resulting composition to the keratinous fibres,
    the composition is left to stand,
    the fibres are rinsed.

The aqueous composition can be simply water.

The aqueous composition can optionally comprise at least one polar solvent. Mention may be made, among polar solvents which can be used in this composition, of organic compounds which are liquid at ambient temperature (25° C.) and at least partially miscible with water.

Mention may more particularly be made, as example, of the alkanols such as ethyl alcohol or isopropyl alcohol, aromatic alcohols, such as benzyl alcohol and phenylethyl alcohol, or also polyols or polyol ethers, such as, for example, ethylene glycol monomethyl, monoethyl or monobutyl ethers, propylene glycol and its ethers, such as, for example, propylene glycol monomethyl ether, butylene glycol, dipropylene glycol, and diethylene glycol alkyl ethers, such as, for example, diethylene glycol monoethyl ether or monobutyl ether.

More particularly, if one or more solvents are present, their respective content in the aqueous composition varies from 0.5 to 20% by weight and preferably from 2 to 10% by weight, with respect to the weight of the said aqueous composition.

Preferably, the aqueous composition does not comprise hydrogen peroxide.

If, however, it comprises it, the concentration by weight of hydrogen peroxide is from 2 to 12% of hydrogen peroxide, preferably from 2 to 6%.

It can additionally comprise agents which stabilize hydrogen peroxide, such as, in particular, sodium pyrophosphate, sodium stannate and sodium salicylate.

When the said aqueous composition comprises hydrogen peroxide, it preferably exhibits a pH of less than 7. The acidic pH guarantees the stability of the hydrogen peroxide in the composition. It can be obtained using acidifying agents, such as, for example, hydrochloric acid, acetic acid, ethydronic acid, phosphoric acid, lactic acid or boric acid, and it can be conventionally adjusted by addition either of basifying agents, such as, for example, ammonia, monoethanolamine, diethanol-amine, triethanolamine, isopropanolamine, 1,3-diamino-propane, an alkali metal or ammonium (bi)carbonate, an organic carbonate, such as guanidine carbonate, or alternatively an alkaline hydroxide, it being possible, of course, for all these compounds to be taken alone or as a mixture.

Whether or not it comprises hydrogen peroxide, the aqueous composition can additionally comprise preservatives, colorants, fragrances, antifoaming agents and sequestering agents, such as, for example, ethylenediaminetetraacetic acid (EDTA) or pentasodium pentatate (CTFA name).

Furthermore, it can be provided in the form of a solution, of an emulsion or of a gel.

Generally, the degree of dilution of the composition according to the invention is such that the resulting composition can be easily applied to the keratinous fibres to be coloured while remaining localized at the spot where it has been applied, in order to avoid the problems caused by runoffs of composition from the area to be treated.

More particularly, the degree of dilution (anhydrous composition/aqueous composition; ratio expressed by weight) is between 2/1 and 1/10.

The pH of the resulting mixture is usually between 7 and 12. Preferably, the pH of the said mixture is usually between 7.5 and 11.

Once the mixing had been carried out in order to produce the ready-for-use composition, the latter is applied to the dry or wet human keratinous fibres.

The leave-in time is generally of the order of one minute to one hour, preferably from 10 minutes to 30 minutes.

The temperature during the process is conventionally between ambient temperature (between 15 and 25° C.) and 80° C., preferably between ambient temperature and 60° C.

On conclusion of the treatment, the human keratinous fibres are optionally rinsed with water, washed with a shampoo, again rinsed with water and then dried or left to dry.

The examples which follow serve to illustrate the invention without, however, limiting the scope thereof.

EXAMPLE 1

The following composition is prepared:

| Ingredients | Amounts (% g) |
|---|---|
| Sodium metasilicate | 10 |
| Ammonium chloride | 3 |
| EDTA | 1 |
| Sodium carboxymethyl cellulose | 5 |
| Diethylhexyl sodium sulphosuccinate and sodium benzoate | 3 |
| Sodium lauryl sulphate | 8 |
| Ascorbic acid | 0.2 |
| para-Phenylenediamine | 0.73 |
| meta-Aminophenol | 0.11 |
| 2-Methyl-5-hydroxyethylaminophenol | 1.1 |
| Glycol distearate | 12.86 |
| PVP/$H_2O_2$ (Peroxydone K30) | 15 |
| Liquid paraffin | 15 |
| Lanolin | 25 |

This paste is mixed at ambient temperature with water by diluting I part by weight of paste with 2 parts by weight of water.

The resulting composition is applied to a lock of natural hair comprising 90% of white hairs at ambient temperature for a time of 30 minutes.

On conclusion of the leave-in time, the lock is rinsed with water, then washed with a standard shampoo, rinsed again and then dried.

A lock purplish in colour is obtained.

EXAMPLE 2

| Ingredients | Amounts (% g) |
|---|---|
| Sodium silicate | 15 |
| Ammonium chloride | 3 |
| EDTA | 1 |
| Sodium carboxymethyl starch (Primogel) | 1 |
| Xanthan gum | 3 |
| Steareth-100/PEG-136/HDI copolymer | 3 |

-continued

| Ingredients | Amounts (% g) |
|---|---|
| Sodium lauryl sulphate | 5 |
| Magnesium stearate | 4 |
| Ascorbic acid | 0.2 |
| para-Phenylenediamine | 0.73 |
| meta-Aminophenol | 0.11 |
| 2-Methyl-5-hydroxyethylaminophenol | 1.1 |
| Glycol distearate | 7.86 |
| PVP/$H_2O_2$ (Peroxydone K30) | 15 |
| Isopropyl myristate | 20 |
| Lanolin | 20 |

This paste is mixed at ambient temperature with water by diluting 1 part by weight of paste with 2 parts by weight of water.

The resulting composition is applied to a lock of natural hair comprising 90% of white hairs at ambient temperature for a time of 30 minutes.

On conclusion of the leave-in time, the lock is rinsed with water, then washed with a standard shampoo, rinsed again and then dried.

A lock purplish in colour is obtained.

EXAMPLE 3

| Ingredients | Amounts (% g) |
|---|---|
| Sodium disilicate | 33.12 |
| Sodium metasilicate | 1.8 |
| Ammonium chloride | 3.5 |
| Sodium carbonate | 5.7 |
| EDTA | 0.7 |
| Clay | 5.5 |
| Carbopol ET2020 (sold by Noveon) | 6.9 |
| Sodium carboxymethyl starch (Primogel, sold by Avebe) | 4.1 |
| Sodium cetearyl sulphate | 2.7 |
| Magnesium stearate | 4.1 |
| Polyvinylpyrrolidone | 4.1 |
| Titanium oxide | 4.1 |
| Polyquaternium-22 | 0.3 |
| PVP/$H_2O_2$ (Peroxydone K30, sold by ISP) | 20.7 |
| para-Phenylenediamine | 1 |
| mete-Aminophenol | 0.15 |
| 2-Methyl-5-(β-hydroxyethyl) aminophenol | 1.5 |
| Lanolin | 25 |

This composition, in the powder form, is mixed with water with a weight of composition/weight of water ratio of 1/2.

It is subsequently applied to locks of hair comprising 90% of white hairs or light brown hairs for 30 minutes at ambient temperature.

On conclusion of the treatment, the locks are rinsed with water and then dried.

Locks of hair dyed with a highlight which is purplish in colour are obtained.

The invention claimed is:

1. An anhydrous composition for the coloring of human keratinous fibers, comprising:
    at least one oxidation dye precursor;
    at least one complex of hydrogen peroxide and of a polymer comprising at least one vinyl heterocyclic monomeric residue; and
    at least one alkaline agent.

2. The anhydrous composition according to claim 1, wherein said anhydrous composition is in the form of a paste.

3. The anhydrous composition according to claim 1, wherein the at least one oxidation dye precursor is chosen from benzene compounds.

4. The anhydrous composition according to claim 1, wherein said anhydrous composition is in a pulverulent form.

5. The anhydrous composition according to claim 1, wherein the at least one vinyl heterocyclic monomeric residue is chosen from N-vinyl monomers.

6. The anhydrous composition according to claim 1, wherein the at least one vinyl heterocyclic monomeric residue is vinylpyrrolidone.

7. The anhydrous composition according to claim 1, wherein, in the at least one complex, the molar ratio of the at least one vinyl heterocyclic monomer to the hydrogen peroxide ranges from 0.5:1 to 2:1.

8. The anhydrous composition according to claim 1, wherein the at least one complex comprises from 10 to 30% by weight of hydrogen peroxide relative to the total weight of the complex.

9. The anhydrous composition according to claim 1, wherein the at least one alkaline agent is chosen from ammonia, silicates, phosphates, hydrogenphosphates, carbonates and hydrogencarbonates of alkali metals, and of alkaline earth metals.

10. The anhydrous composition according to claim 1, wherein the at least one alkaline agent is chosen from alkali metal silicates and carbonates.

11. The anhydrous composition according to claim 1, comprising from 0.1% to 50% by weight of the complex of hydrogen peroxide and of a polymer, with respect to the total weight of the composition.

12. A method for coloring human keratinous fibers, comprising:
applying to the keratinous fibers a composition, wherein the composition is obtained by mixing an anhydrous composition with an aqueous composition;
said anhydrous composition comprising:
at east one oxidation dye precursor;
at least one complex of hydrogen peroxide and of a polymer comprising at least one vinyl heterocyclic monomeric residue; and
at least one alkaline agent,
leaving the composition to stand, and
rinsing the fibers.

13. The method according to claim 12, wherein the aqueous composition does not comprise hydrogen peroxide.

14. The method according to claim 12, wherein the aqueous composition comprises water.

15. The method according to claim 12, wherein the aqueous composition comprises hydrogen peroxide in an amount ranging from 2% to 12% by weight, relative to the total weight of the aqueous composition.

* * * * *

UNITED STATES PATENT AND TRADEMARK OFFICE
CERTIFICATE OF CORRECTION

PATENT NO. : 7,799,095 B2
APPLICATION NO. : 12/215422
DATED : September 21, 2010
INVENTOR(S) : Maud Mario, Patricia Desenne and Jean-Marie Millequant It is certified that error appears in the above-identified patent and that said Letters Patent is hereby corrected as shown below:

Claim 2, col. 24, line 67, "an hydrous" should read --anhydrous--.

Claim 12, col. 26, line 11, "at east" should read --at least--.

Signed and Sealed this

Fourteenth Day of December, 2010

David J. Kappos
*Director of the United States Patent and Trademark Office*